Figure 1:
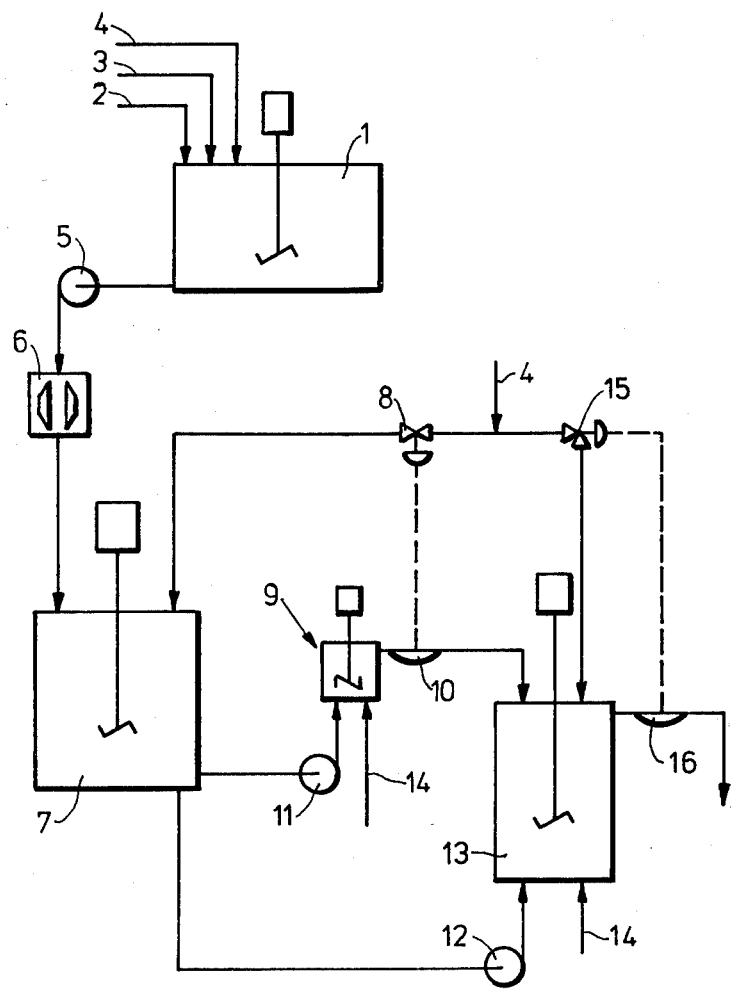

United States Patent [19]

Breig et al.

[11] 4,233,213
[45] Nov. 11, 1980

[54] PROCESS FOR THE CONTINUOUS INDIRECT DIAZOTIZATION OF AROMATIC AMINES

[75] Inventors: Kurt Breig; Georg Dehmel, both of Cologne; Norbert Hamm, Bergisch-Gladbach, all of Fed. Rep. of Germany

[73] Assignee: Bayer Aktiengesellschaft, Leverkusen, Fed. Rep. of Germany

[21] Appl. No.: 939,153

[22] Filed: Sep. 1, 1978

[30] Foreign Application Priority Data

Sep. 17, 1977 [DE] Fed. Rep. of Germany ....... 2741925

[51] Int. Cl.$^3$ ............................................ C07C 113/00
[52] U.S. Cl. .................................................... 260/141
[58] Field of Search ..................................... 260/141 P

[56] References Cited

U.S. PATENT DOCUMENTS

| Re. 19,645 | 7/1935 | Hancock et al. | 260/141 P X |
|---|---|---|---|
| 3,117,954 | 1/1964 | Hupfer | 260/141 P |
| 3,423,391 | 1/1969 | Kindler et al. | 260/141 P |

*Primary Examiner*—Paul F. Shaver
*Attorney, Agent, or Firm*—Sprung, Felfe, Horn, Lynch & Kramer

[57] ABSTRACT

Fluctuations in concentration of the starting materials during continuous diazotization are taken into account by passing a component stream from the receiver to the diazotization vessel through an analyser where, for a short residence time, the nitrite content is determined by an electrochemical measuring technique. A required nitrite excess is adjusted in the receiver on the basis of this measurement. By virtue of the pH-value, however, a diazotization reaction still does not take place in the receiver.

7 Claims, 2 Drawing Figures

PROCESS FOR THE CONTINUOUS INDIRECT DIAZOTIZATION OF AROMATIC AMINES

This invention relates to a process for the continuous indirect diazotization of aromatic amines, particularly weakly basic amines, for example containing nitro groups, wherein the amine is mixed with water and an excess of nitrite in a receiver and the resulting mixture is pumped into a diazotization vessel where it reacts with a mineral acid.

Continuous diazotization is described for example in German Auslegeschrift No. 1,231,251. An aqueous amine suspension or a mineral-acid amine-salt suspension flows into the diazotization vessel together with a nitrite solution and a mineral acid. The disadvantage of the continuous process described in the above-mentioned Publication, particularly in the case of weakly basic amines, is that, in the event of fluctuations in concentration in the starting materials, there prevails alternately a nitrite excess and a nitrite deficit, and, in the event of a nitrite deficit, those fractions of amine which are not immediately diazotized react with the diazo compound to form a diazo-amine compound. These secondary reactions adversely affect the quality and yield of the dye or intermediate product being produced.

By virtue of the process according to the present invention, it is possible to obtain an improvement in product quality in a continuous operation by passing a component stream from the receiver to the diazotization vessel through an analyser, the residence time in the analyser being shorter than in the diazotization vessel by a factor of at least 3, determining in the analyser by an electrochemical measuring technique the point in time at which a value characteristic of the amine in question exceeds or falls below a critical level and subsequently introducing nitrite into the receiver until the characteristic value again falls below or exceeds the critical level in the analyser. Accordingly, the present invention provides a continuous process for indirect diazotization in which the required nitrite excess is controlled by means of an electrochemical measuring technique not in the actual diazotization vessel, but instead in a receiver which is maintained at a pH-value at which no diazotization reaction takes place. A disturbance-free "indirect diazotization" is thus obtained in the diazotization vessel because the amine can actually be introduced into the mineral acid with the required nitrite concentration. The analyser installed in the path of the component stream between the receiver and the diazotization vessel readily responds to fluctuations in the concentration of amines in the receiver as a function of time which are therefore unable to disturb the overall reaction in the diazotization vessel.

The expression "indirect diazotization" is generally used for a procedure in which an excess of nitrite is first added to the amine, followed by addition to a mineral acid.

The process is preferably carried out in such a way that the characteristic value in the analyser corresponds to a nitrite excess in the receiver of from 1% to 10%, preferably 2%.

A process in which the characteristic value is potentiometrically, voltametrically or polarographically determined is particularly preferred.

The process is described by way of example in the following and is diagrammatically illustrated in FIG. 1.

Figure 2:
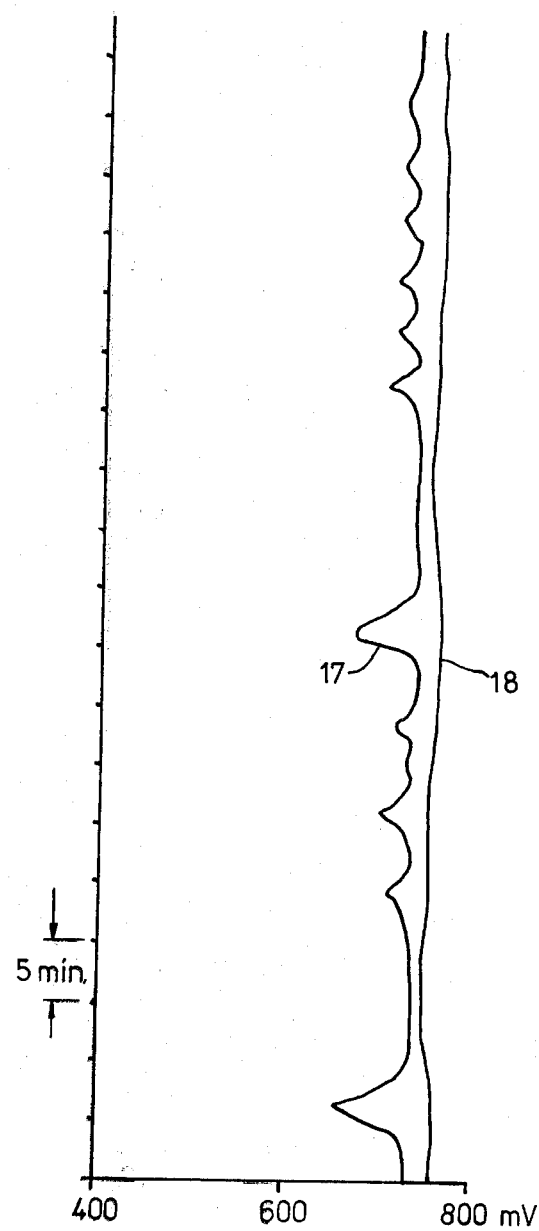

FIG. 2 shows fluctuations in potential in the analyser and in the diazotization vessel.

An amine 2 to be diazotized is mixed with water 3 and nitrite 4 in a receiver 1. The quantity of nitrite in 1 should amount to between 50% and 95% and preferably to 90% of the necessary quantity of nitrite. It is immaterial whether the receiver 1 is filled continuously through metering units or in batches. The "mashed" amine suspension is delivered by a pump 5 into the receiver 7, optionally through a size-reducing machine 6. A size-reducing machine 6 is particularly necessary in the case of coarsely crystalline amines. Toothed colloid mills, corundum disc mills or bead mills are suitable. Additional nitrite 4 is delivered into the receiver 7 through a valve 8. Nitrite 4 should be present in excess in the receiver 7, the excess normally amounting to between 1% and 10% and preferably to 2% of the stoichiometrically necessary quantity of nitrite. The addition of nitrite 4 to the receiver 7 is controlled from an analyser 9. The analyser 9 measures the nitrite concentration of the amine suspension or solution running off from the receiver 7 by an electrochemical measuring device 10 (e.g. using a redox potentiometry technique, voltametry or polarography). It is adjusted so that, in the event of a nitrite deficit, nitrite 4 is delivered to the receiver 7 through 8 and, once the required excess has been reached and measured at 10, the addition of 4 through 8 is stopped. Only a relatively small quantitative stream 11 is normally pumped through the analyser 9. Most of the amine suspension from the receiver 7 is delivered into the diazotization vessel 13 through the pump 12. By adding mineral acid 14 to 9 and 13, the amine suspension is quantitatively diazotized. An additional monitoring facility in the form of an electrochemical measuring device 16, similar in structure to 10, is present at the outlet of 13 where it also measures the nitrite excess. It is only in exceptional cases that the device 16 initiates the introduction of nitrite 4 into the vessel 13 through the valve 15. Such a case may arise, for example, during the start-up phase.

The residence time in the diazotization vessel 13 has to be adapted to the amine. The residence time is defined as the quotient of the active volume of the vessel and the volumetric flow per unit of time. In most cases, the residence time is between 2 and 10 minutes. By comparison with the residence time in 13, the residence time in 9 has to be smaller than in 13 by a factor of at least 3. It is surprising that a factor of only 3 or 4 between the residence time in 9 and 13 is sufficient to keep the required nitrite excess in 13 constant.

FIG. 2 shows a typical recorder graph of the signals 17 and 18 released from 10 and 16. In this example, the redox potential is measured in 10 and 16. Both measuring stations are adjusted to the same sensitivity. In the analyser 9, the potential fluctuates considerably. In the diazotization vessel 13, a substantially constant nitrite excess is maintained by the procedure according to the invention.

EXAMPLE

Diazotization of 2-nitro-4-methyl aniline 1670 parts of 2-nitro-4-methyl aniline were suspended in 2300 parts of water and 2300 parts of sodium nitrite solution (30 g/100 ml) in the receiver 1. The quantity of nitrite corresponds to 90% of the quantity theoretically required for complete diazotization. The suspension passed through a corundum disc mill 6 into the receiver 7. The quantitative flow through the analyser 9, which has a volume of 0.2 liter, amounted to 5.2 l/h. The residence time was 2.3 minutes. An analyzer of this size is also suitable for use on a commercial scale. In a test installation, however, the main stream through the pump 12 is considerably smaller than it would be on an industrial scale, so that, for simulation on a pilot scale, this stream has to be reduced accordingly in order to obtain the required residence times in the vessels. The residence time in the vessel 13 amounts to approximately 7 minutes. The nitrite excess at the measuring stations 10 and 13 is determined by redox potential measurement. The measuring stations are equipped with platinum and silver/silver chloride electrodes. 35% hydrochloric acid is pumped into the vessels 9 and 13. In this example, the vessels 7, 9 and 13 are kept at temperatures of 5°, 30° and 20° C. by cooling with brine. The diazotized product flowing off from the diazotization vessel 13 is directly further processed after filtration with active carbon.

FIG. 2 shows the recorded readings 17 and 18 of 10 and 16.

It is possible similarly to subject other aromatic amines to continuous diazotization, for example 2-chloro-4-nitroaniline, 4-chloro-2-nitraniline, 2-methoxy-4-nitraniline, 3,3'-dichlorobenzidine, 2,5-dichloro-4-sulphanilic acid, aniline mono- and di-sulphonic acids, aminonaphthalene sulphonic acids, p-nitraniline, dichloroaniline and 1-amino-2-hydroxy-5-chlorobenzene-3-sulphonic acid.

What we claim is:

1. A process for the continuous indirect diazotization of an aromatic amine which comprises mixing an aromatic amine with water and an excess of nitrite in a receiving zone in which no diazotization occurs, primarily feeding the mixture from the receiving zone to a diazotization vessel thereafter reacting the resulting mixture in the diazotization vessel with a mineral acid, withdrawing a component stream of the mixture of amine, water and nitrite from the receiving zone into an analyser, the residence time of the component stream in the analyser being shorter by a factor of at least 3 than the residence time of the mixture in the diazotization vessel, and adding additional nitrite to the receiving zone in an amount determined by the amount of amine present in the mixture which is monitored in the analyser.

2. A process for the continuous indirect diazotization of an aromatic amine which comprises mixing an aromatic amine with water and an excess of nitrite in a receiving vessel in which no diazotization occurs, primarily feeding the mixture from the reaction vessel to a diazotization vessel; thereafter reacting the resulting mixture in the diazotization vessel with a mineral acid, withdrawing a component stream of the mixture of amine, water and nitrite from the receiving vessel and passing same to the diazotization vessel through an analyser, wherein the residence time of the mixture is shorter in the analyser than in the diazotization vessel by a factor of at least 3, determining the analyser by electrochemical measurement the point in time at which a value characteristic of the particular amine exceeds or falls below a critical level and subsequently introducing additional nitrite into the receiver until the characteristic value again reaches the critical level in the analyser.

3. A process as claimed in claim 1 or 2, wherein the amine is a weakly basic amine.

4. A process as claimed in claim 3, wherein the amine contains nitro groups.

5. A process as claimed in claims 1 or 2, wherein the characteristic value in the analyser corresponds to a nitrite excess in the receiving vessel of from 1 to 10%.

6. A process as claimed in claim 5, wherein the nitrite excess in the receiving vessel is 2%.

7. A process as claimed in claim 2, wherein the characteristic value is determined one of potentiometrically, voltametrically or polarographically.

* * * * *